United States Patent
Imai et al.

(10) Patent No.: US 6,877,512 B2
(45) Date of Patent: Apr. 12, 2005

(54) AIRWAY DEVICE

(75) Inventors: Ayako Imai, Davis, CA (US); Eugene P. Steffey, Davis, CA (US); Pamela H. Eisele, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 161 days.

(21) Appl. No.: 09/948,029

(22) Filed: Sep. 5, 2001

(65) Prior Publication Data

US 2003/0041862 A1 Mar. 6, 2003

(51) Int. Cl.[7] ............................................. A61M 16/00
(52) U.S. Cl. .......................... 128/207.15; 128/207.14; 128/200.26
(58) Field of Search ................. 128/207.14, 207.15, 128/207.16, 207.17, 207.18, 204.18, 200.26; 604/96.01, 101.01, 101.02, 101.03, 101.05, 102.01, 102.02, 102.03; 602/192, 194

(56) References Cited

U.S. PATENT DOCUMENTS

| | | | | |
|---|---|---|---|---|
| 3,443,564 A | * | 5/1969 | Oehmig .................. | 128/207.14 |
| 3,734,094 A | * | 5/1973 | Calinog ...................... | 600/380 |
| 4,090,518 A | * | 5/1978 | Elam ...................... | 128/207.15 |
| 4,263,921 A | * | 4/1981 | Trugillo ...................... | 600/549 |
| 4,509,514 A | | 4/1985 | Brain | |
| 4,737,153 A | * | 4/1988 | Shimamura et al. ........ | 604/526 |
| 4,796,615 A | * | 1/1989 | Bullock et al. ........ | 128/202.27 |
| 5,038,766 A | * | 8/1991 | Parker ................... | 128/200.26 |
| 5,303,697 A | | 4/1994 | Brain | |
| 5,305,740 A | * | 4/1994 | Kolobow ................ | 128/207.14 |
| 5,309,906 A | * | 5/1994 | LaBombard ............ | 128/207.14 |
| 5,339,805 A | * | 8/1994 | Parker ................... | 128/200.26 |
| 5,499,625 A | | 3/1996 | Frass et al. | |
| 5,743,258 A | * | 4/1998 | Sato et al. ............. | 128/207.15 |
| 5,819,733 A | * | 10/1998 | Bertram ................. | 128/207.15 |
| 5,865,176 A | * | 2/1999 | O'Neil ................... | 128/207.15 |
| 5,873,362 A | | 2/1999 | Parker | |
| 5,937,859 A | | 8/1999 | Augustine et al. | |
| 5,937,861 A | | 8/1999 | Augustine | |
| 6,148,818 A | * | 11/2000 | Pagan ................... | 128/207.15 |
| 6,196,225 B1 | | 3/2001 | Allgeyer | |
| 6,386,199 B1 | * | 5/2002 | Alfery ................... | 128/207.15 |
| 6,390,093 B1 | | 5/2002 | Mongeon | |
| 6,626,169 B2 | * | 9/2003 | Gaitini ................. | 128/200.14 |
| 2002/0170556 A1 | * | 11/2002 | Gaitini ................. | 128/200.14 |

FOREIGN PATENT DOCUMENTS

WO  WO8907956  * 8/1999

OTHER PUBLICATIONS

Soykan, Orhan, et al, Ventricular Evoked Response Measurements from Pacing Electrodes, 1995, www.biomed.m-tu.edu/osoykan/ariticles/19995/19995.htm.*

Fujita, Michio, et al, Use of Laryngeal Mask Airway in Small Animals, 1991, J. Vet. Med. Sci., vol. 53(6), pp. 1081, 1092.*

JS Kim, et al., "Endoesophageal Intubation for Controlled Ventilation in Rabbits: A Rapid and Easy Technique to Establish a Patent Airway", abstract only. Contemporary Topics, American Association for Laboratory Animal Science, Jul. 2000, p. 80, vol. 39, No. 4.

(Continued)

Primary Examiner—Henry Bennett
Assistant Examiner—Mital Patel
(74) Attorney, Agent, or Firm—Townsend and Townsend and Crew LLP

(57) ABSTRACT

An airway device is disclosed. The airway device includes a tubular structure including a first end region having a first opening and a second end region having a second opening. A mask is in the tubular structure and the mask defines the first opening. An inflatable balloon is proximate to the first end region of the tubular structure, and a pilot tube can be in communication with the inflatable balloon.

33 Claims, 6 Drawing Sheets

OTHER PUBLICATIONS

A. I. J. Brain, et al., "The laryngeal mask airway. Development and preliminary trials of a new type of airway", The Association of Anaesthetists of Gt Britain and Ireland, (1985), pp. 356–361, vol. 40.

Michio Fujita, et al., "Use of Laryngeal Mask Airway in Small Animals", J. Vet. Med. Sci., (1991), pp. 1081–1082, vol. 53, No. 6.

Dee Horne, et al., "A Nonrebreathing Anesthetic Delivery System for Mice", Lab Animal, Technique, Jul./Aug. 1998, pp. 32–34, vol. 27, No. 7.

Vijayalakshml U. Patil, MD, et al., "Use of the Laryngeal Mask Airway for Emergency or Elective Airway Management Situations in Pigs", Contemporary Topics, The American Association for Laboratory Animal Science, Nov. 1997, pp. 47–49, vol. 36, No. 6.

Takashi Asai, M.D., PH.D., "Use of the Laryngeal Mask Airway in Laboratory Cats", Anesthesiology, Laboratory Report, (1998), pp. 1680–1682, vol. 88, No. 6.

ML Cruz, et al., "Use of a laryngeal mask for airway maintenance during inhalation anaesthesia in rabbits", Veterinary Anaesthesia and Analgesia, Jul. 2000, pp. 115–116, vol. 27, No. 2.

A. I. J. Brain, "The Laryngeal Mask—A New Concept in Airway Management", British Journal of Anaesthesia, (1983), pp. 801–805, vol. 55.

José R.C. Braz, M.D., PH.D., et al., "Investigation Into the Use of the Laryngeal Mask Airway in Pentobarbital Anesthetized Dogs", Veterinary Anesthesia, (1999), pp. 502–505, vol. 28.

"Flex–Tip Endotracheal Tube", www.parkemedical.com/PET.htm Jun. 7, 2001 (print date), 4 pgs.

"IN / Intubation Equipment", www.999ambulance.co.uk/it380037.htm, Jun. 7, 2001 (print date), 4 pgs.

"How Does the LMA Work?", www.Imaco.com/htm/body__how__does__it__work.html, (2000), 2 pgs.

"Airway Management and Intubation Equipment", www.ic-c.cc.il.us/haps/respiratory/equip–ami.htm, Jun. 7, 2001 (print date), 10 pgs.

* cited by examiner

AIRWAY DEVICE

CROSS-REFERENCES TO RELATED APPLICATIONS

Not applicable.

STATEMENT AS TO RIGHTS TO INVENTIONS MADE UNDER FEDERALLY SPONSORED RESEARCH OR DEVELOPMENT

Not applicable.

BACKGROUND OF THE INVENTION

A wide variety of airway devices are used to provide gas (e.g., oxygen) to a mammal's airway. Examples of airway devices include face masks, endotracheal tubes, and laryngeal devices.

A face mask covers the mouth and nose of a patient. Face masks are non-invasive, since the sealing of the airway is accomplished not by penetration into the patient's airway, but by covering the mouth and nose of the patient. However, airway patency is not assured since the tongue and other structures can still obstruct the airway. Also, it is difficult to maintain a seal of the airway for any period of time, particularly during positive pressure ventilation. Leakage around the face mask results in ineffective ventilation and, during anesthesia, contaminates the operating room with anesthetic gases. Furthermore, a face mask does not prevent the introduction of air into the esophagus and stomach (gastric insufflation) or protect against the aspiration of stomach contents (e.g., breathing of vomited material).

Endotracheal tubes are inserted through the mouth or nose and into the trachea (the windpipe) where a cuff surrounding the tube seals against the interior surface of the trachea. This approach avoids the deficiencies of face masks because it includes a conduit traversing the pharynx, and forms an effective seal against the airway, allowing positive pressure ventilation, and protection against the aspiration of stomach contents.

While solving several problems, endotracheal tubes create new challenges. They are difficult to insert and position properly within the trachea, almost always requiring a laryngoscope, stylet or other intubation aid. Penetration of the larynx and trachea is invasive and is a highly noxious stimulus requiring anesthesia. Furthermore, once in place or even during the insertion process, endotracheal tubes can injure the delicate tissue of the larynx and trachea including the vocal cords. In some instances, endotracheal tubes can cause bleeding, swelling, laryngospasms, patient discomfort and hoarseness. Incorrect positioning of the tip of an endotracheal tube (distally into the mainstem bronchi or proximal dislocation out of the trachea) is an additional concern.

Another type of airway device is a laryngeal airway device. Laryngeal airway devices provide a more direct supply of gas to the trachea than a face mask and are not inserted into the trachea. One type of laryngeal device has an air tube with proximal and distal ends and a padded, sealing member that is attached to the distal end of the air tube. The sealing member can be made of a closed cell foam or can be inflatable. In both instances, the sealing member is in the form of a spoon-shaped cuff that surrounds a hole that provides air to the trachea. When this type of laryngeal airway device is used, the sealing member is seated in the throat of the mammal and the hole in the sealing member is in communication with the distal end of the air tube. Air is supplied to the trachea through the air tube and through the hole in the sealing member.

While the described laryngeal airway device addresses some of the concerns of face masks and the described endotracheal tubes, a number of other problems remain. For example, the padded, sealing member of the described laryngeal airway device is relatively large. The mammal using the laryngeal airway device may be small (e.g., less than 10 pounds) and it may be difficult to insert the sealing member into the mouth and down the throat of the small mammal. It can also be difficult to properly position the air hole in the sealing member over the larynx. It is also difficult to position the sealing member so that it is lodged in the esophagus to stop any fluids (e.g., gastric juices) from coming up from the stomach. Furthermore, the wide sealing member can sometimes cause the epiglottis to fold and block the larynx, thus inhibiting lung ventilation. The wide sealing member can also injure the larynx and obstruct the mammal's airway, especially when it becomes dislocated within the mammal's throat.

Accordingly, improved airway devices and methods for using the same would be desirable. Embodiments of the invention address these and other problems.

SUMMARY OF THE INVENTION

Embodiments of the invention include airway devices, and methods for using such airway devices.

One embodiment of the invention is directed to an airway device comprising: a) a tubular structure including a first end region having a first opening and a second end region having a second opening; b) a mask in the tubular structure, wherein the mask defines the first opening; c) an inflatable balloon proximate the first end region of the tubular structure; and d) a pilot tube in communication with the inflatable balloon, wherein the first opening is positioned between the second opening and the inflatable balloon.

Another embodiment of the invention is directed to an airway device comprising: a) a tubular structure including a first end region having a mask that defines a first opening and a second end region having a second opening, wherein the mask covers a larynx of a mammal when the tubular structure is inserted in a mouth of the mammal; b) an inflatable balloon proximate the first end region of the tubular structure, wherein the inflatable balloon substantially blocks an entrance to an esophagus of the mammal when the balloon is inflated, and wherein the first opening and the mask are between the second opening and the inflatable balloon; and c) a pilot tube in communication with the inflatable balloon, wherein the pilot tube supplies gas to inflate the inflatable balloon.

Methods of using the above-described airway devices are also disclosed. In one exemplary embodiment, the inflatable balloon of the airway device is inserted into the mouth of a mammal and into the esophagus of the mammal. The balloon is inflated so that the inflated balloon substantially blocks off the esophagus. Gas is supplied to the trachea through the tubular structure. The gas passes into the trachea of the mammal via an opening in a mask that is in tubular structure.

These and other embodiments of the invention are described in further detail below.

DETAILED DESCRIPTION

Figure 1:
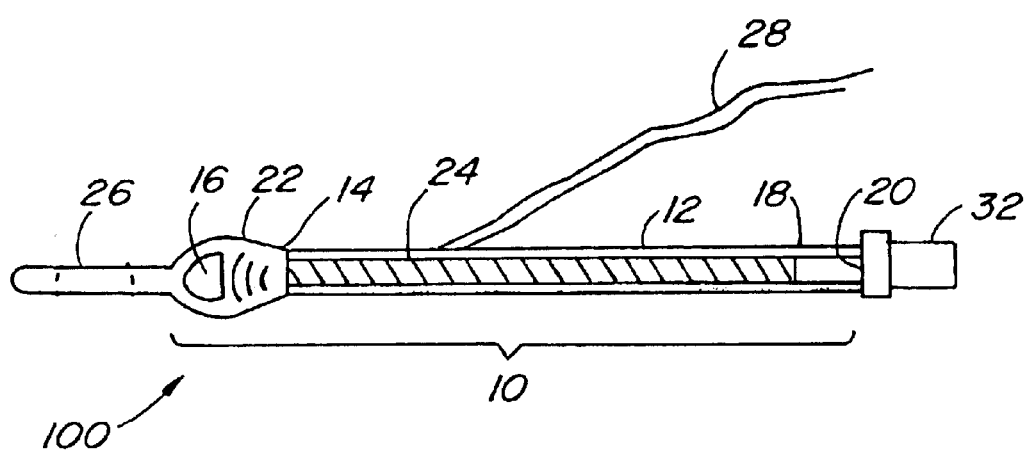
FIG. 1 shows an airway device according to an embodiment of the invention with a partial cut away view.

The airway devices according to embodiments of the invention are typically used in mammals. The mammals can be humans or animals. Examples of such mammals include infants (premature or full term), toddlers, and animals such as rabbits, mice, dogs, cats, etc. As will be explained in further detail below, embodiments of the invention are particularly well suited for use with small mammals. Small mammals typically have a weight less than about 10 pounds (e.g., less than about 6 pounds). Examples of small mammals include rabbits, mice, infants, puppies, kittens, rats, ferrets, etc.

As noted above, one embodiment of the invention is directed to an airway device comprising a tubular structure. The tubular structure includes a first end region having a first opening and a second end region having a second opening. A mask is in the tubular structure and defines the first opening. An inflatable balloon is proximate the first end region of the tubular structure. A pilot tube is in communication with the inflatable balloon to provide gas that inflates the balloon. In embodiments of the invention, the first opening and the mask are positioned between the second opening and the inflatable balloon.

When the inflatable balloon is inserted into the esophagus, the balloon can be inflated to substantially block off the esophagus. The blockage inhibits contents from the stomach from passing upward in the esophagus and into the trachea. At the same time, the inflated balloon is secured to the inner walls of the esophagus, consequently securing the airway device to the mammal's throat.

When the airway device is secured, the mask lies above and covers the larynx and the laryngeal opening to the mammal's trachea. In some embodiments, the first opening formed by the mask is larger than, and is positioned over, the larynx so that the larynx can receive the maximum amount of gas. Gas passes through a gas passage in the tubular structure and out of the first opening and into the trachea of the mammal. In this regard, the tubular structure may serve as a conduit for respiratory gases to (and also from) the trachea. The mask defining the first opening is generally a wide, open structure that directs the gas passing through the gas passage to the trachea. Additionally, the mask can cover the larynx of a mammal so that the backflow of gas coming out of the first opening and passing out of the mammal's mouth is minimized. The airway devices according to embodiments of the invention can form a continuous airway to the trachea.

Embodiments of the invention have a number of advantages over the above-described conventional airway devices. For example, in comparison to face masks, embodiments of the invention can be inserted directly into the throat of a mammal. The tongue, for example, does not obstruct the passage of gas to and from the mammal's trachea. Also, in comparison to face masks, in embodiments of the invention, the inflated balloon blocks contents from the stomach from passing up the esophagus and into the trachea.

In comparison to endotracheal tubes, the components of the airway devices according to embodiments of the invention need not be inserted into the trachea of a mammal. Accordingly, contact with the trachea walls, and the sensitive tissue of the larynx is minimized or avoided. As a consequence, problems such as bleeding, swelling, laryngospasms, patient discomfort, and hoarseness are also minimized or avoided. Also, because inserting an air tube into the trachea is not necessary in embodiments of the invention, the insertion and subsequent securing of the airway device to the mammal can be done "blindly", without intubation aids such as a laryngoscope. This is particular helpful in the case of small mammals where the use of intubation aids is difficult or impossible due to the small size of the mammal's mouth.

The airway devices according to embodiments of the invention are generally smaller than the sealing member-type laryngeal devices described above, even when the sealing members are of the inflatable variety. Accordingly, the airway devices according to embodiments of the invention are more easily inserted, and are therefore much better suited for use with small mammals than the sealing member-type laryngeal devices. Additionally, because the airway devices according to embodiments of the invention use a balloon to substantially block off the esophagus, the balloon can be inflated to the size that is appropriate for the particular mammal being treated. In embodiments of the invention, one airway device could be effectively used with many different types of mammals. In addition, since the mask forms a relatively large opening, it is much easier to properly position the mask over the laryngeal opening and the trachea than it is to position a small hole in a sealing member over the laryngeal opening and the trachea. The relatively large opening provides room for the epiglottis to move in natural fashion and also does not cause the epiglottis to be pushed down over the larynx.

FIG. 1 shows an airway device 100 according to an embodiment of the invention. The airway device 100 includes a tubular structure 10 and a balloon 26. A pilot tube 28 is in communication with the balloon 26. Gas (e.g., air) is supplied though the pilot tube 28 to inflate the balloon 26. Gas can also be removed through the pilot tube 28 to deflate the balloon 26. A device such as a syringe (not shown) can supply pressurized gas to the pilot tube 28. The material forming the balloon 26 is generally an elastomeric material that can expand upon the application of pressure and retract in the absence of applied internal pressure.

The balloon 26 may be in any suitable form. For example, the balloon 26 may expand radially outward about an axis after receiving pressurized gas. In this example, the inflated balloon may be cylindrically shaped. Alternatively, the balloon 26 may expand radially outward about a point to form an inflated sphere. In FIG. 1, the expandable portion of the balloon 26 (in its unexpanded state) is shown by dotted lines.

In the illustrated embodiment, the tubular structure 10 and the balloon 26 may appear as a single integral structure. That is, the outer surfaces of the tubular structure 10 and the balloon 26 may have a common outer material (e.g., silicone), and the airway device 100 may appear as one integral structure when viewed by the user. In other embodiments, it is possible to have a clear demarcation between the tubular structure 10 and the balloon 26 (as when the tubular structure 10 and the balloon 26 are bonded together with an intervening adhesive).

The tubular structure 10 includes a first end region 14, a second end region 18, and a main portion 12 that lies between the first end region 14 and the second end region 18. In this example, the first and second end regions 14, 18, are at respective, opposite ends of the tubular structure 10. A first opening 16 is present at the first end region 14 and a second opening 20 is present at the second end region 18. The first opening 16 may be larger than the second opening 20. The first opening 16 and the second opening 20 form ends of a gas passage that passes through the tubular structure 10. Gas that passes through this gas passage is supplied to (or removed from) the lungs and the trachea of a mammal.

An optional spiral wire 24 may be present in the tubular structure 10 to provide structural reinforcement for the tubular structure 10. Materials such as silicone may be quite flaccid. A structural reinforcing member such as a spiral wire 24 can provide the tubular structure 10 with sufficient stiffness and flexibility so that the tubular structure 10 can be easily inserted into the throat of a mammal, while maintaining an open gas passage within the tubular structure 10. The spiral wire 24 can also ensure that the gas passage in the tubular structure 10 remains open as the tubular structure is manipulated (e.g., bent). The spiral wire 24 can be embedded within the wall of a tubular structure 10, or could be placed adjacent to the inside wall of the tubular structure 10. The pitch of the windings of the spiral wire 24 may be adjusted as desired to obtain the desired degree of reinforcement. Suitable materials for the spiral wire 24 include stainless steel and tungsten.

A mask 22 is incorporated in the tubular structure 10. In typical embodiments, the mask 22 has a shape that is adapted to fit over the larynx of the mammal. The mask 22 defines the wide, first opening 16 through which gas passes to and from the tubular structure 10. The first opening 16 in the mask 22 ensures that gas can be delivered to or received from the trachea of the mammal. The mask 22 may be integrally formed with the main portion 12 of the tubular structure 10 or may be separately formed and then joined together.

As shown in FIG. 1, the mask 22 and the first opening 16 are disposed between the balloon 26 and the second opening 20 of the tubular structure 10. In embodiments of the invention, the area of the airway device 100 that is between the first opening 16 and the second opening 20 is free of a balloon. Also, the balloon 26 may be spatially separated from the mask 22 and the first opening 16 formed by the mask 22. The particular arrangement of the balloon 26, the mask 22, the first opening 16, and the second opening 20 allows the balloon 26 to be inserted into the esophagus of the mammal while the mask 22 and the first opening 16 are in communication with the laryngeal opening.

After insertion, the entire balloon 26 can be completely within the esophagus. Once the balloon 26 is inserted into the esophagus of the mammal, the mask 22 is positioned over, and covers, the larynx of the mammal. Unlike the above-described endotracheal tubes, in embodiments of the invention, the lungs of the mammal can be ventilated without contacting the vocal cords of the larynx. The balloon 26, when inflated, can substantially block off the esophagus while the tubular structure 10 provides a patent airway to the trachea (not shown) via the first opening 16.

An adaptor 32 can be disposed at the second end region 18 of the tubular structure 10 and can be inserted into the second opening 20. The adaptor 32 can be made of, for example, any suitable polymeric material. It can also be structured (e.g., with internal or external threads) so that the airway device 100 can be coupled to an external gas source (not shown). Examples of external gas sources include oxygen tanks, air pumps (manual or automatic), anesthetic gas sources, etc.

Each of the parts of the airway device may have any suitable dimensions. Preferably, the parts of the airway device and the airway device as a whole may be sized so that they are configured for use with a small mammal. In some embodiments (e.g., for small mammals), the external diameter of the main portion 12 of the tubular structure 10 can be about 20, or even about 10 millimeters or less. The length of the tubular structure 10 can be about 20 centimeters, or even about 10 centimeters or less. The maximum cross-sectional area of the mask 22 or the area of the first opening 16 defined by the mask 22 can be less than about 2.0 cm×.2.0 cm (height×width), or even about 1.0 cm×.1.0 cm (height× width). For example, the mask may have a cross-sectional dimension of about 1.5 cm×1.0 cm (height×width) in some embodiments.

Factors such as the size of the mammal's esophagus, the size of the mammal's larynx, the size of the mammal's mouth, etc. may influence the particular size of the various parts of the airway device. For example, for an adult New Zealand White Rabbit, the aperture defined by the mask may have dimensions of about 1.5 cm×1.0 cm (height×width). The length of the tubular structure of the device may be about 12 cm or less, and the external diameter of the main portion of the tubular structure may be 6.5 mm while the internal diameter of the main portion of the tubular structure may be about 5.0 mm.

Each of the parts of the airway device may be made of any suitable material. Typically, one or more parts of the airway device are made of medical grade plastic materials. Exemplary materials include polyvinyl chloride, silicone rubber, polyurethanes, etc. Non-traumatizing materials such as silicone rubbers are preferred (if portions of the airway device come into contact with the mammal's internal tissue). Thus, in some embodiments, the tubular structure (including the mask) and the balloon comprise silicone rubber. All surfaces that could contact the mammal's internal tissue may comprise soft, silicone rubber.

The embodiment shown in FIG. 1 can be formed in any suitable manner. In one exemplary process, a polymeric coating may be formed on a mandrel and dried. A wire may then be wound around the dried polymeric coating. Another polymeric coating may be superimposed on the wire to form a tube wall and embed the spiral wire within the tube wall to form a main portion of the tubular structure. A mask may then be molded according to conventional molding process and then may be bonded to the main portion of the tubular structure. Before or after bonding the mask to the main portion of the tubular structure, a balloon and its associated pilot tube can be bonded to the mask. Heat, pressure, and/or solvents can be used to bond the parts of the airway device together. Those of ordinary skill in the art can determine specific bonding and molding conditions.

Figure 2:
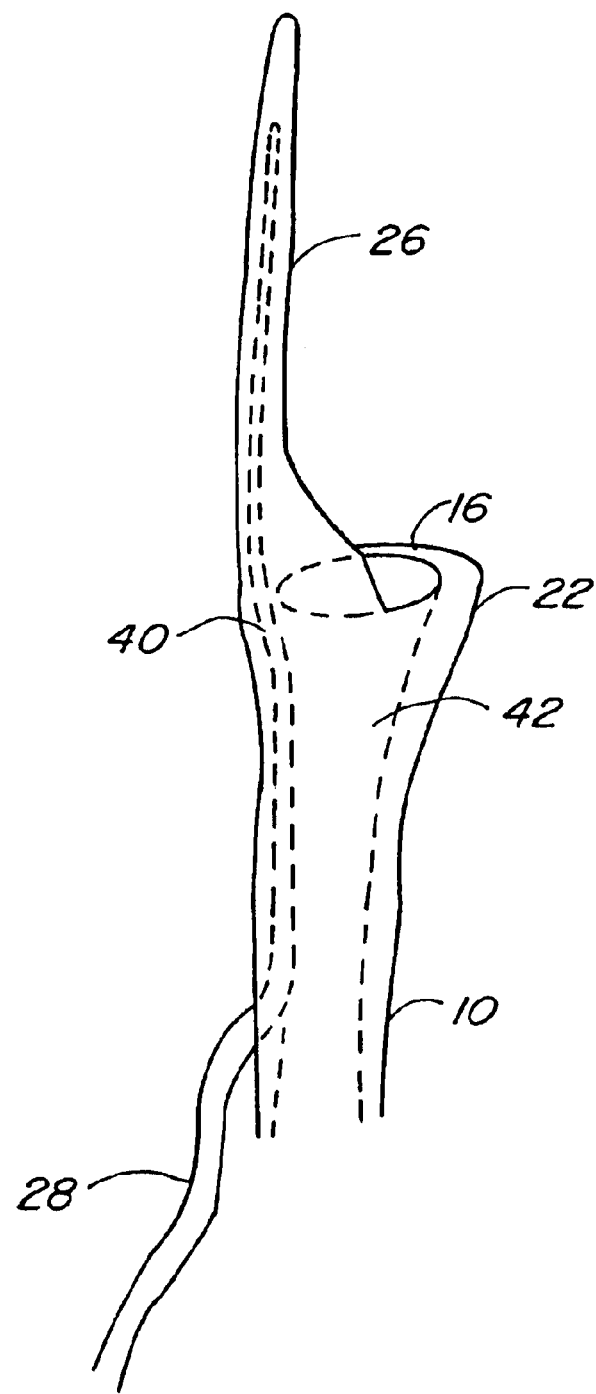
FIG. 2 shows a portion of an airway device according to an embodiment of the invention with gas passages shown in invisible lines.

FIG. 2 shows a portion of an airway device according to an embodiment of the invention. As shown in FIG. 2, a pilot tube 28 can define a gas passage 40 that continues internally in the tubular structure 10 to the balloon 26. Gas from the pilot tube 28 is used to inflate the balloon 26.

Figure 3:
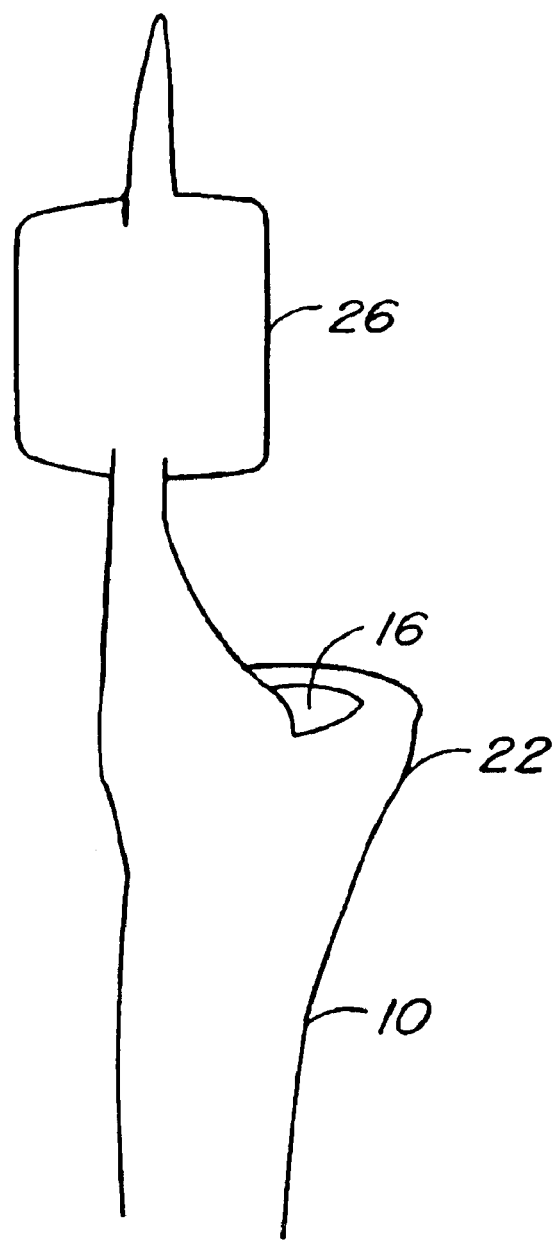
FIG. 3 shows a portion of an airway device according to an embodiment of the invention when the balloon is inflated.

As shown in FIG. 3, after gas is supplied to the balloon 26 via the pilot tube 28, the balloon 26 can expand in a radially outward direction. The radially outwardly expanding balloon 26 can substantially block an entrance region of an esophagus (not shown). By blocking the entrance region of an esophagus, contents from the stomach of the mammal (e.g., gastric juices) are prevented from passing out of the esophagus and into the trachea (not shown). Also, the inflated balloon fixes the position of the airway device within the mammal's throat.

Referring again to FIG. 2, the gas passage 42 that is used to supply a gas such as oxygen to the trachea and lungs of a mammal can end at the first opening 16. The mask 22 may define the first opening 16. The first opening 16 can be relatively larger in cross-sectional area than the cross-sectional area of the gas passage in the main portion of the tubular structure and also larger in cross-sectional area than the second opening (not shown) in the tubular structure 10. As shown in FIG. 2, the cross-sectional area of the gas passage 42 may generally gradually increase towards the first opening 16. In FIG. 2, the first opening 16 is shown as being generally perpendicular to the tubular structure 10. The first opening 16 could also be angled with respect to the orientation of the tubular structure 10.

Figure 4:
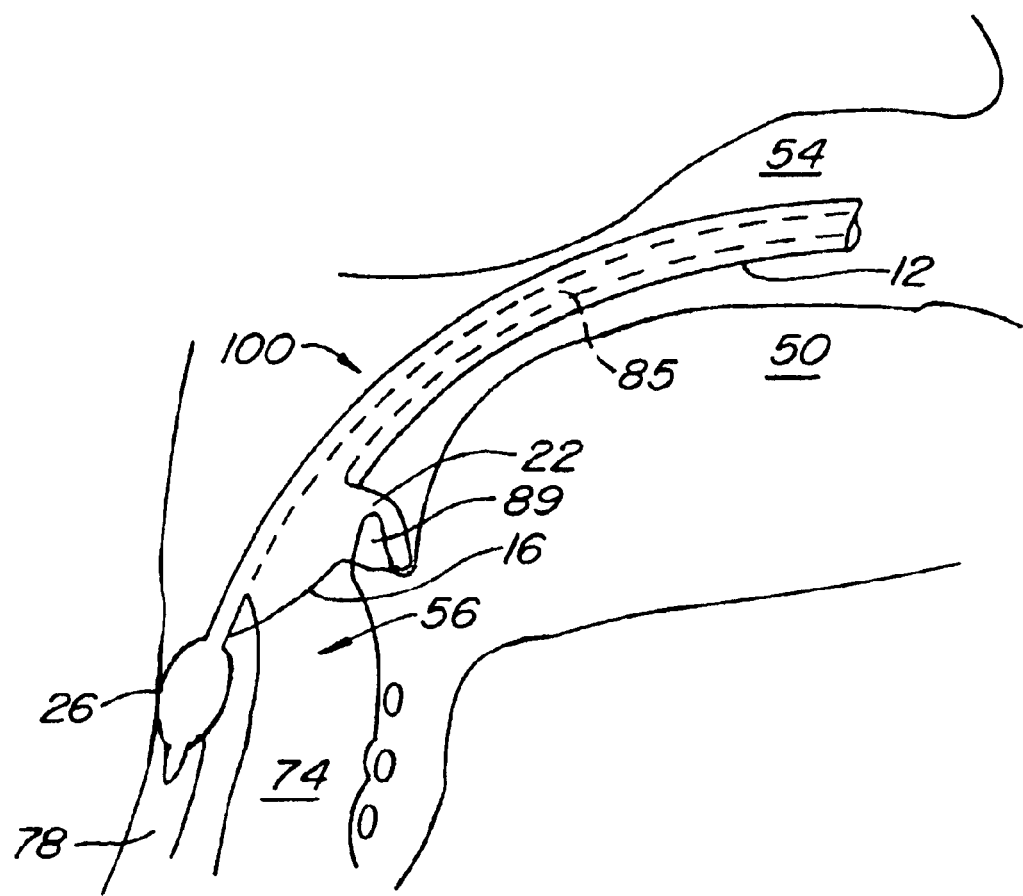
FIG. 4 shows an airway device according to an embodiment of the invention when it is used to supply gas to the trachea of a mammal.

FIG. 4 shows how the airway device 100 can be used when it is inserted into the mouth of a mammal. In FIG. 4, the main portion 12 of the tubular structure of the airway device 100 is in the mouth 54 and above the tongue 50 of a mammal. The main portion 12 has a gas channel 85 that ends at a first opening 16 defined by a mask 22. An inflated balloon 26 coupled to the mask 22 substantially blocks off the entrance of the esophagus 78.

When the airway device 100 is secured in the throat of a mammal, the mask 22 that is positioned above the balloon 26 covers the larynx 56. One end of the mask 22 is positioned under and at the base of the epiglottis 89. As shown in FIG. 4, it is not likely that the epiglottis 89 will fold to obstruct the larynx 56 and block the passage to the trachea 74. The large first opening 16 of the mask 22 allows the epiglottis 89 to be positioned inside the mask 22 so that it can retract to the position that it is normally in when the mammal is breathing.

As shown in FIG. 4, good communication is provided between the trachea 74 and the first opening 16 so that gas (e.g., oxygen) can freely pass through the gas passage in the tubular structure 10, out of the first opening 16, and into the trachea 74. Gas can also pass from the trachea 74 into the first opening 16 and into the tubular structure 10.

Figure 5:
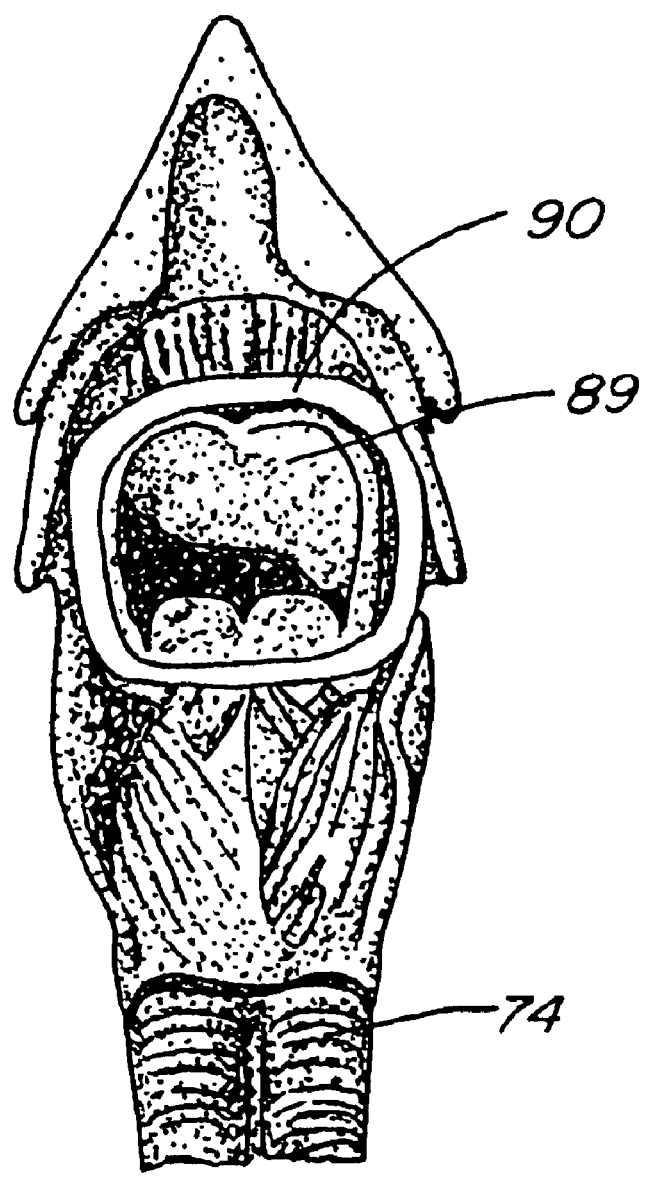
FIG. 5 shows a portion of the larynx and the trachea with a highlighted region that can be sealed by a mask.

The mask 22 may be configured so that it forms an effective seal around the larynx. For example, as shown in FIG. 5, a mask (not shown) can contact tissue behind the epiglottis 89 and may seal off the region 90 around the epiglottis 89 to provide gas (e.g. oxygen) to the trachea 74. The mask 22 may also be cooperatively structured with respect to the shape of the larynx 56. In this regard, it is possible to size the mask 22 to fit around the larynx of a mammal of a particular size and/or species.

Other embodiments and variations to the embodiments described above are possible. For example, referring to FIG. 4, instead of or addition to passing gas through the tubular structure 10 via the first opening 16, an optical microscope could be fed through the tubular structure 10 and into the trachea 74 to examine the trachea 74. In another example, a gas sensor could be disposed in the vicinity of the mask 22 and could detect levels of, for example, carbon dioxide coming from the lungs of the mammal. Wires (not shown) for the gas sensor could pass through the tubular structure 10.

Figure 6:
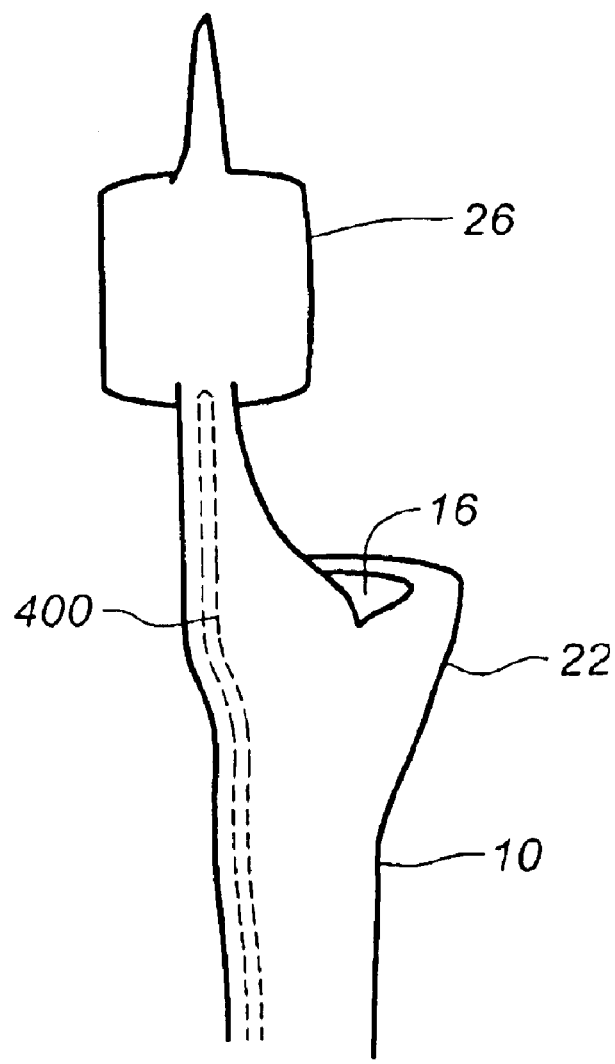
FIG. 6 shows a portion of an airway device according to an embodiment of the invention with a monitoring device.

Other elements could be added to the airway device in the vicinity of the balloon 26. Referring to FIG. 6, a monitoring device 400 (shown in dotted lines) could be included in the tubular structure 10 or could be attached to the tubular structure 10. For example, an esophageal stethoscope and/or a thermometer could be included in the airway device in the vicinity of the balloon 26 and coupled to the tubular structure 10. The electrodes for an electrocardiogram could also be added to the airway device in the vicinity of the balloon. Optical or electrical conduits for such elements could be fed through the tubular structure 10. Esophageal stethoscopes and/or thermometers can be used, for example, to monitor the mammal during general anesthesia. In yet other embodiments, the airway device according to embodiments of the invention could provide access to tho trachea for tracheal lavage or for instillation of medications or test compounds (e.g., in research animals) into the trachea.

While the foregoing is directed to certain preferred embodiments of the present invention, other and further embodiments of the invention may be devised without departing from the basic scope of the invention. Such alternative embodiments are intended to be included within the scope of the present invention. Moreover, the features of one or more embodiments of the invention may be combined with one or more features of other embodiments of the invention without departing from the scope of the invention. For example, although the specifically illustrated airway devices shown in FIGS. 1 to 4 do not specifically show additional monitoring elements such as gas sensors, microscopes, and stethoscopes, it is understood that any of the specifically described airway devices shown in FIGS. 1 to 4 could include any suitable monitoring element and can still be within the scope of the invention.

What is claimed is:

1. An airway device comprising:
    a) a tubular structure including a first end region having a first opening and a second end region having a second opening;
    b) a mask in the tubular structure, wherein the mask defines the first opening wherein the mask is adapted to cover a larynx of a mammal when the tubular structure is inserted in a mouth of a mammal;
    c) an inflatable balloon proximate the first end region of the tubular structure; and
    d) a pilot tube in communication with the inflatable balloon,
    wherein the first opening is positioned between the second opening and the inflatable balloon, and
    wherein a proximal end of the balloon is distal to the first opening at the first end region of the tubular structure, and
    wherein the region of the tubular structure between the first opening and the second opening is free of a balloon.

2. The airway device of claim 1 wherein the tubular structure comprises a spiral wire.

3. The airway device of claim 1 wherein the mask is configured to fit over the larynx of a mammal that weighs less than about 10 pounds.

4. The airway device of claim 1 wherein the tubular structure and the inflatable balloon are formed as one integral structure.

5. The airway device of claim 1 further comprising an adaptor coupled to the second end region of the tubular structure.

6. The airway device of claim 1 wherein the airway device comprises a medical grade plastic material.

7. The airway device of claim 1 wherein the tubular structure includes an external diameter, and wherein the external diameter of the tubular structure is less than about 10 mm.

8. The airway device of claim 1 wherein the balloon or the tubular structure comprises a medical grade plastic material.

9. The airway device of claim 1 wherein the inflatable balloon is sized so that it is capable of being inserted into the mouth of a pre-mature infant.

10. A method of using the airway device of claim 1 comprising:
  a) inserting the inflatable balloon into the esophagus of a mammal so that the first opening is proximate a larynx of the animal; and
  b) inflating the balloon so that the inflated balloon substantially blocks the esophagus.

11. The method of claim 10 wherein the mammal weighs less than about 10 pounds.

12. The method of claim 10 wherein the mammal is an infant.

13. The method of claim 10 further comprising:
  supplying gas to lungs in the mammal through the tubular structure.

14. The method of claim 10 further comprising:
  supplying anesthetic gas to lungs in the mammal through the tubular structure.

15. An airway device comprising:
  a) a tubular structure including a first end region having a mask that defines a first opening and a second end region having a second opening, wherein the mask is adapted to cover a larynx of a mammal when the tubular structure is inserted in a mouth of the mammal;
  b) an inflatable balloon proximate the first end region of the tubular structure wherein the inflatable balloon substantially blocks an entrance to an esophagus of the mammal when the balloon is inflated, and wherein the first opening and the mask are between the second opening and the inflatable balloon, and wherein a proximal end of the balloon is distal to the first opening at the first end region of the tubular structure; and
  c) a pilot tube in communication with the inflatable balloon, wherein the pilot tube supplies gas to inflate the inflatable balloon,
  wherein the region of the tubular structure between the first opening and the second opening is free of a balloon.

16. The airway device of claim 15 wherein the tubular structure comprises a spiral wire.

17. The airway device of claim 15 wherein the mask wherein the tubular structure, the mask, and the inflatable balloon are formed as one integral structure.

18. The airway device of claim 15 further comprising an adaptor at the second end region of the tubular structure.

19. The airway device of claim 15 wherein the mask is adapted to cover a larynx of the mammal, and wherein the mammal weighs less than about 10 pounds.

20. The airway device of claim 15 wherein the tubular structure includes an external diameter less than about 10 mm.

21. A method of using the airway device of claim 15 comprising:
  a) inserting the inflatable balloon and the mask into the mouth of the mammal and into the esophagus of the mammal;
  b) inflating the balloon so that the esophagus is substantially blocked off by the inflated balloon; and
  c) supplying gas through the tubular structure and into the trachea of the mammal.

22. The method of claim 21 wherein the mammal weighs less than about 10 pounds.

23. The airway device of claim 1 further comprising:
  a monitoring device coupled to the balloon.

24. The airway device of claim 23 wherein the monitoring device is a gas sensor.

25. The airway device of claim 23 wherein the monitoring device comprises electrodes for an electrocardiogram.

26. The airway device of claim 23 wherein the monitoring device comprises a thermometer.

27. An airway device comprising:
  a) a tubular structure including a first end region having a mask that defines a first opening and a second end region having a second opening, wherein the mask is adapted to cover a larynx of a mammal when the tubular structure is inserted in a mouth of the mammal;
  b) a inflatable balloon proximate the first end region of the tubular structure, wherein the inflatable balloon substantially blocks an entrance to an esophagus of the mammal when the balloon is inflated, and wherein the first opening and the mask are between the second opening and the inflatable balloon, mid wherein a proximal end of the balloon is distal to the first opening at the first end region of the tubular structure;
  c) a pilot tube in communication with the inflatable balloon, wherein the pilot tube supplies gas to inflate the inflatable balloon; and
  d) a monitoring device coupled to the inflatable balloon,
  wherein the region of the tubular structure between the first opening and the second opening is free of a balloon.

28. The airway device of claim 27 wherein the monitoring device is a gas sensor.

29. The airway device of claim 27 wherein the monitoring device comprises electrodes for an electrocardiogram.

30. The airway device of claim 27 wherein the monitoring device comprises a thermometer.

31. A method of using the airway device of claim 27 comprising:
  a) inserting the inflatable balloon and the mask into the mouth of the mammal and into the esophagus of the mammal;
  b) inflating the balloon so that the esophagus is substantially blocked off by the inflated balloon;
  c) supplying gas through the tubular structure and into the trachea of the mammal; and
  d) monitoring the mammal using the monitoring device.

32. The method of claim 31 wherein the gas comprises anesthetic gas, and wherein during monitoring, the mammal is anesthetized.

33. The method of claim 31 wherein monitoring comprises monitoring the temperature of the mammal.

* * * * *